US00PP09972P

United States Patent [19]

Svejda et al.

[11] Patent Number: Plant 9,972

[45] Date of Patent: Jul. 22, 1997

[54] SHRUB ROSE PLANT NAMED 'ROYAL EDWARD'

[75] Inventors: Felicitas J. Svejda, Nepean; Ian S. Ogilvie, Pointe Claire, both of Canada

[73] Assignee: Her Majesty the Queen in right of Canada, as represented by the Minister of Agriculture, Ottawa, Canada

[21] Appl. No.: 662,758

[22] Filed: Jun. 10, 1996

[51] Int. Cl.[6] ..... A01H 5/00

[52] U.S. Cl. ..... Plt./1

[58] Field of Search ..... Plt./1, 26, 27, Plt./9

*Primary Examiner*—Howard J. Locker

*Attorney, Agent, or Firm*—Burns, Doane, Swecker & Mathis, L.L.P.

[57] ABSTRACT

A new and distinct variety of shrub rose plant is provided which forms in clusters attractive pink blossoms that tend to lighten somewhat when fully open. The new variety exhibits a distinctive semi-dwarf and spreading growth habit with glossy foliage, and good winter hardiness. Resistance to powdery mildew and blackspot has been observed. The new variety propagates well by the use of softwood stem cuttings, and is well adapted for growing as colorful ornamentation in the landscape. It is particularly well suited for use in rock gardens and small space plantings.

2 Drawing Sheets

SUMMARY OF THE INVENTION

The new variety of shrub rose plant of the present invention was created by artificial pollination at the Central Experimental Farm, Ottawa, Ontario, Canada. The female parent (i.e., the seed parent) was *Rosa kordesii* and the male parent (i.e., the pollen parent) was the U32 line (non-patented in the United States). The female parent was derived from a spontaneous chromosome doubling of a hybrid between *Rosa rugosa* and *Rosa wichuraiana*. The male parent originated from a cross between *Rosa kordesii* and a hybrid derived from an open-pollinated cross between 'Red Dawn' (non-patented in the United States) and 'Suzanne' (non-patented in the United States) and the climber 'Zeus' (non-patented in the United States). The high degree of winter hardiness is derived from *Rosa kordesii* Wulff, *Rosa laxa* Retzius, and *Rosa spinosissima* L.

It was found that the new variety of shrub rose plant of the present invention possesses the following combination of characteristics:

(a) exhibits a semi-dwarf and spreading growth habit with attractive dark green glossy foliage,
(b) forms in clusters attractive pink blossoms that tend to lighten when fully open,
(c) propagates well by the use of softwood cuttings,
(d) exhibits good winter hardiness, and
(e) is particularly well suited for growing as ornamentation in the landscape.

The rose plants can be grown well on their own roots out-of-doors without protection at L'Assomption, Quebec, Canada. The blossoms commonly appear in large quantities during June and repeat at a lesser intensity until late September. Resistance to powdery mildew and substantial resistance to blackspot have been exhibited.

When compared to 'Louis Jolliet' (U.S. Plant Pat. No. 9,222), the new variety of the present invention exhibits fewer blossom petals and forms a smaller plant. It can be considered to be the first semi-miniature spreading winter-hardy rose.

The new variety well meets the needs of the horticultural industry. It can be grown to advantage as attractive ornamentation in parks, gardens, public areas, and residential landscapes. It is well suited for growing in the landscape, and is particularly well suited for use in rock gardens and small space plantings.

The characteristics of the new variety have been found to be homogenous and stable and have been shown to be strictly transmissible by asexal propagation by the rooting of softwood stem cuttings conducted at L'Assomption, Quebec, Canada.

The new variety has been named the 'Royal Edward'.

BRIEF DESCRIPTION OF THE PHOTOGRAPHS

The accompanying photographs show, as nearly true as it is reasonably possible to make the same in color illustrations of this character, typical specimens of plants and plant parts of the new variety. The rose plants of the new variety described herein were approximately 5 to 6 years of age and were photographed while growing on their own roots at L'Assomption, Quebec, Canada.

DETAILED DESCRIPTION

Figure 1:
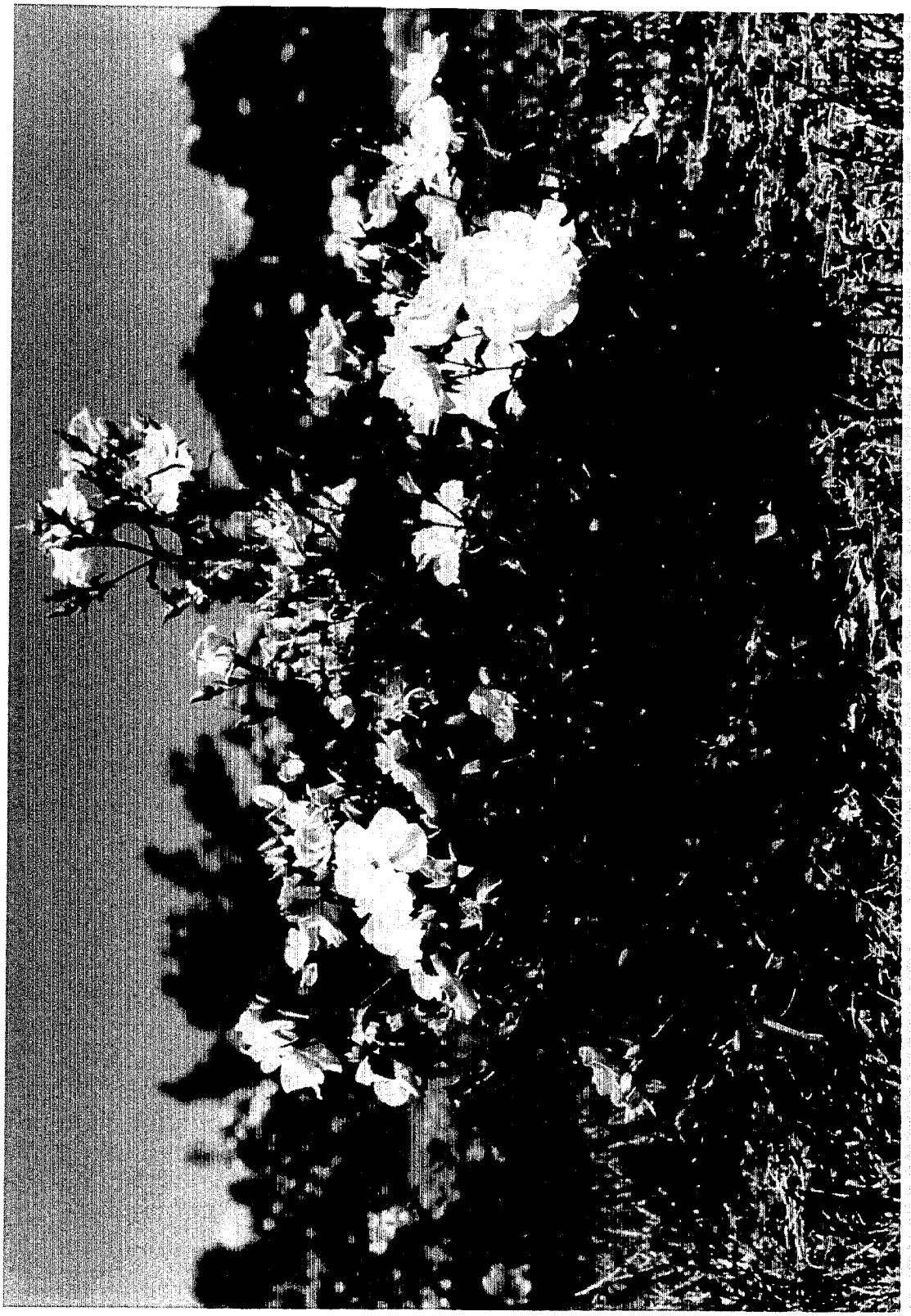
FIG. 1 illustrates a typical flowering plant of the new variety while growing in the landscape. The semi-dwarf spreading growth habit, abundant dark green glossy foliage, and pink blossoms are apparent.
Figure 2:
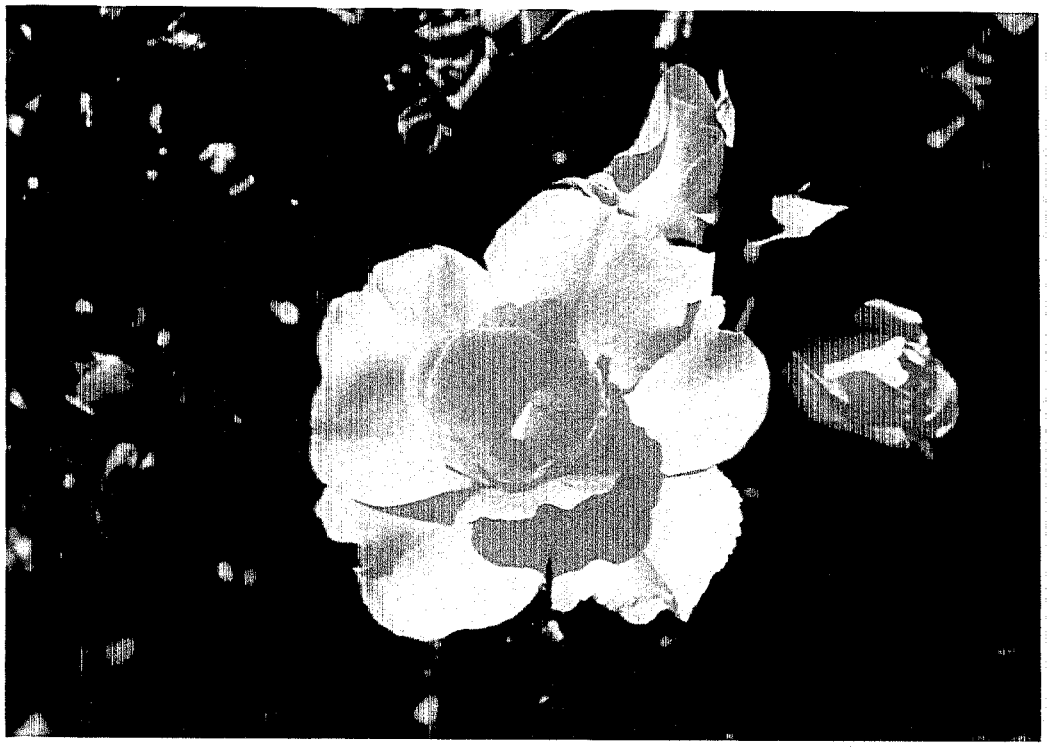
FIG. 2 illustrates typical specimens of a newly opened blossom, opening buds, and foliage of the new variety.

The chart used in the identification of colors is that of The Royal Horticultural Society (R.H.S. Colour Chart). Common color terms are to be accorded their ordinary dictionary significance. The description is based on the observation of 5 to 6 year-old plants of the new variety while being grown outdoors at L'Assomption, Quebec, Canada.

Class: Shrub.

Plant:

*Height.*—A five year-old plant commonly assumes a height of approximately 0.45 m.

*Width.*—A five year-old plant commonly assumes a width of approximately 0.55 m.

*Habit.*—Semi-dwarf (i.e., semi-miniature) and spreading.

Thorns:

*Quantity.*—Approximately 5±2 thorns per 100 mm. of stem on average.

Leaves: Compound and pinnate.

*Leaflets.*—Number: commonly 3, 5 or 7. Frequency: abundant. Shape: ovate and acuminate. Margins: dentate. Size: commonly approximately 40 mm. in length on average and approximately 22 mm. in width on average. Texture: leathery. General appearance: dark green, and glossy.

*Color.*—Adult foliage: dark green, Yellow-Green Group 147A on upper surface and Yellow-Green Group 147B on under surface. Young foliage: some reddish tinge commonly is visible.

Inflorescence:

*Number of flowers.*—Commonly in clusters of 1 to 7.

*Peduncle.*—Erect, as shown in FIG. 1.

*Sepals.*—Configuration: broad as shown in FIG. 1.

*Buds.*—Shape: ovoid before the opening of the sepals, as shown in FIG. 1. Color upon opening: the outer petals are deep pink.

*Flower.*—Shape: tends to flatten when fully open as shown in FIG. 1. Diameter: approximately 55 mm. on average. Color (when blooming): medium pink, Red Group 55B on the upper and under surfaces. The coloration of the blossoms commonly fades to a pale pink when the blossoms are fully mature. The petals have a yellow spot at the base, Green-Yellow Group ID. Fragrance: slight. Petal number: approximately 18±2 on average. Petal drop: petals tend to detach fairly clearly. Fertility: flowers are of low fertility and under open pollination only occasionally form hips. *Lasting quality: the blossoms commonly last* 3 to 5 days when cut and placed in a vase and generally last longer on the plant. The blossom life is influenced by temperature and other environmental conditions that are encountered.

Development:

*Vegetation.*—Good vigor.

*Blossoming.*—In large quantities during June with repetition at a lesser intensity until late September.

*Hardiness.*—Has survived test winters to −35° C. without protection except for natural snow with only slight winter injury .

*Resistance to diseases.*—Is resistant to powdery mildew [*Sphaerotheca pannosa* (Wallr. ex Fr.) Lev.] and is largely resistant blackspot (*Diplocarpon rosae* Wolf.) during observations to date.

*Preferred mode of propagation.*—The use of softwood cuttings to produce self-rooted plants is recommended. For instance, softwood cuttings taken at the bud stage can be dipped in rooting powder (e.g., Stimroot No. 2, 0.4 percent indolebutyric acid of Plant Products, Bramalea, Ontario, Canada) and placed under mist for 3 to 4 weeks at 20° to 25° C. ambient temperature.

We claim:

1. A new and distinct variety of shrub rose plant characterized by the following combination of characteristics:

(a) exhibits a semi-dwarf and spreading growth habit with attractive dark green glossy foliage,
(b) forms in clusters attractive pink blossoms that tend to lighten when fully open,
(c) propagates well by the use of softwood cuttings,
(d) exhibits good winter hardiness, and
(e) is particularly well suited for growing as ornamentation in the landscape;

substantially as herein shown and described.

* * * * *